US012349886B2

United States Patent
Mizuno et al.

(10) Patent No.: US 12,349,886 B2
(45) Date of Patent: Jul. 8, 2025

(54) RETRACTOR

(71) Applicants: MOCHIDA PHARMACEUTICAL CO., LTD., Tokyo (JP); NATIONAL UNIVERSITY CORPORATION HOKKAIDO UNIVERSITY, Sapporo (JP)

(72) Inventors: Hitoshi Mizuno, Tokyo (JP); Kuniyoshi Masuda, Tokyo (JP); Masahiko Katayama, Tokyo (JP); Tomokazu Takai, Tokyo (JP); Toshiya Endo, Tokyo (JP); Norimasa Iwasaki, Hokkaido (JP); Tomohiro Onodera, Hokkaido (JP); Koji Iwasaki, Hokkaido (JP)

(73) Assignees: MOCHIDA PHARMACEUTICAL CO., LTD., Tokyo (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 339 days.

(21) Appl. No.: 17/792,028

(22) PCT Filed: Jan. 13, 2021

(86) PCT No.: PCT/JP2021/000787
§ 371 (c)(1),
(2) Date: Jul. 11, 2022

(87) PCT Pub. No.: WO2021/145333
PCT Pub. Date: Jul. 22, 2021

(65) Prior Publication Data
US 2023/0041137 A1    Feb. 9, 2023

(30) Foreign Application Priority Data

Jan. 14, 2020   (JP) ................. 2020-003606

(51) Int. Cl.
*A61B 17/02*    (2006.01)
(52) U.S. Cl.
CPC .......... *A61B 17/02* (2013.01); *A61B 17/0206* (2013.01)
(58) Field of Classification Search
CPC ......................... A61B 17/02; A61B 17/0206
See application file for complete search history.

(56) References Cited

U.S. PATENT DOCUMENTS 3,470,872 A * 10/1969 Grieshaber ........ A61B 17/0206
606/208
6,152,874 A * 11/2000 Looney .............. A61B 17/0206
600/222
(Continued)

FOREIGN PATENT DOCUMENTS

CN       108498135 A  *  9/2018   ......... A61B 17/0206
JP       2005-27933 A    2/2005
(Continued)

OTHER PUBLICATIONS

English translation of CN 108498135 A (Year: 2018).*
(Continued)

*Primary Examiner* — Julianna N Harvey
(74) *Attorney, Agent, or Firm* — Birch, Stewart, Kolasch & Birch, LLP (57) ABSTRACT

A retractor is provided that can form a joint cavity internal space for a field of view for an endoscope and practice of a treatment in a state where a wound area is spread. A retractor includes first arm portions 2 and 3 and a second arm portion 4 positioned between the first arm portions 2 and 3. The first arm portions 2 and 3 include first claw portions 12 and 13 to be hung on a wound area entrance edge. The second arm portion 4 includes a second claw portion 14 to be hung on the wound area entrance edge. When the first arm portions 2 and 3 and the second arm portion 4 are in a closed state, (Continued)

the first claw portions 12 and 13 and the second claw portion 14 overlap with each other.

10 Claims, 10 Drawing Sheets

(56) References Cited

U.S. PATENT DOCUMENTS

| | | | | |
|---|---|---|---|---|
| 2010/0286485 | A1* | 11/2010 | Valentini | A61B 17/0206 600/224 |
| 2011/0144450 | A1* | 6/2011 | Paolitto | A61B 17/0206 600/224 |
| 2014/0257035 | A1* | 9/2014 | Blain | A61B 17/0218 600/104 |

FOREIGN PATENT DOCUMENTS

| | | |
|---|---|---|
| JP | 3197302 U | 4/2015 |
| JP | 2016-182197 A | 10/2016 |

OTHER PUBLICATIONS

International Search Report (PCT/ISA/210) issued in PCT/JP2021/000787, dated Apr. 6, 2021.
Written Opinion of the International Searching Authority (PCT/ISA/237) issued in PCT/JP2021/000787, dated Apr. 6, 2021.

* cited by examiner

RETRACTOR

TECHNICAL FIELD

The present invention relates to a retractor which abuts a wound area entrance edge of an incised skin tissue and opens the wound area.

BACKGROUND ART

In recent years, as an orthopedic surgery treatment for a patient having a focus in a joint, arthroscopic surgery using an arthroscope has been performed. The arthroscopic surgery has widely been diffused in an orthopedic surgery field for the purpose of reduction in a physical burden on a patient and early recovery after surgery. In this arthroscopic surgery, a focal area is treated by inserting both of dedicated surgical instruments and so forth and an endoscope into a comparatively small wound area in which the epidermis of a knee or an elbow is incised and opened.

In the arthroscopic surgery, a surgeon practices a treatment by using surgical instruments inserted into a joint cavity while checking an endoscopic image by a monitor screen. It is required to secure a joint cavity internal space (hereinafter, referred to as work space) for a field of view for an endoscope and practice of a treatment. Further, in order to smoothly perform insertion of surgical instruments and so forth and an endoscope to a wound area, a retractor is used which maintains the wound area in an open state.

In related art, a forceps-like retractor has been known which has a pair of tip end portions including claw portions to be hung on a wound area entrance edge and operation grip portions for opening and closing those tip end portions (see the following Patent Literature 1).

In this retractor (forceps type retractor), the claw portions in the tip end portions to be inserted into a wound area are in shapes which overlap with each other in a winding manner in a closed state so that insertion into a wound area entrance edge becomes easy.

Further, another forceps type retractor has been known in which each tip end portion is provided with a plurality of claw portions (see the following Patent Literature 2).

This retractor includes a pair of operation grip portions and a pivot portion which rotatably couples both of the operation grip portions together and a pair of arm portions which extend to the respective opposite sides to the operation grip portions via the pivot portion, and the plurality of claw portions are provided on tip end portion of the arm portion.

The plurality of claw portions protrude orthogonally to a direction in which the arm portion extends and are provided to be aligned at intervals among the others in the direction in which the arm extends. Because the plurality of claw portions are provided as described above and the claw portions thereby abut mutually different positions of a wound area entrance edge, a wound area does not linearly extend while being kept closed, and the wound area can be opened.

CITATION LIST

Patent Literature

Patent Literature 1: Japanese Patent Laid-Open No. 2005-27933

Patent Literature 2: Japanese Patent Laid-Open No. 2016-182197

SUMMARY OF INVENTION

Technical Problem

However, in a retractor in the above Patent Literature 1, when an attempt to spread a wound area is made by separating both claw portions from each other in a state where two claw portions are hung on a wound area entrance edge, the wound area linearly extends in an almost closed state, and the wound area cannot widely be opened.

In addition, as for the retractor disclosed in the above Patent Literature 1, a wound area can be opened in a quadrangular shape by using two retractors; however, securing a work space in arthroscopic surgery is not considered, and there is inconvenience where workability in arthroscopic surgery is not proper.

Further, in a retractor disclosed in the above Patent Literature 2, because each claw portion protrudes orthogonally to a direction in which an arm portion extends, when each of the claw portions is deeply inserted into a wound area, the arm portion becomes an obstacle, and hanging of each of the claw portions on a wound area entrance edge becomes shallow. Thus, hanging of each of the claw portions on the wound area entrance edge is easily released.

As described above, as for the retractor disclosed in the above Patent Literature 2, securing a work space in arthroscopic surgery is not considered either, and there is inconvenience where workability in arthroscopic surgery is not proper.

In consideration of the above points, an object of the present invention is to provide a retractor that can easily form a work space for arthroscopic surgery in a state where a wound area is spread.

Solution to Problem

To achieve such an object, a first aspect of the present invention provides a retractor abutting a wound area entrance edge of an incised skin tissue and opening the wound area, the retractor including: a pair of first arm portions which are integrally coupled with each other on base end sides and extend toward tip ends; a single second arm portion which is positioned between the first arm portions, a base end side of the second arm portion being rotatably coupled with the first arm portions via a shaft portion, the second arm portion extending toward a tip end; and operation portions which perform opening and closing operations of the first arm portions and the second arm portion in a case where a state where the first arm portions and the second arm portion overlap with each other is set as a closed state and a state where tip end sides of the first arm portions and of the second arm portion are separated from each other is set as an open state, in which each of the first arm portions includes, in a tip end portion, a first claw portion which protrudes in an opening direction to be hung on the wound area entrance edge, the second arm portion includes, in a tip end portion, a second claw portion which protrudes in an opposite direction to the first claw portion to be hung on the wound area entrance edge, and when the first arm portions and the second arm portion are set to the closed state, the first claw portions and the second claw portion overlap with each other.

The retractor of the first aspect of the present invention includes two first claw portions in the tip end portions of two first arm portions, includes one second claw portion in the tip end portion of one second arm portion, and is thereby provided with three claw portions.

In the closed state, because the second claw portion is housed between the two first claw portions, the three claw portions are comparatively compactly gathered in the tip end portions of the first arm portions and the second arm portion, and insertion into a wound area of an incised skin tissue can smoothly be performed.

When the first arm portions and the second aim portion start opening from the closed state by an operation of the operation portions, the first claw portions and the second claw portion become a hooked state where those are hooked on a wound area entrance edge in respective positions. In this case, because one claw portion is provided on the tip end portion of each of the arm portions, the arm portions do not obstruct a hanging state of each of the claw portions. Moreover, the claw portions protrude in the opening directions of the respective aim portions and thus become a state where those are comparatively deeply hung on the wound area entrance edge.

Furthermore, when the first arm portions and the second arm portion become the open state, the first claw portions and the second claw portion are separated in directions opposite to each other, and the wound area is thereby enlarged. In this case, because two first claw portions and one second claw portion abut the wound area entrance edge at three points, the wound area does not linearly extend while being kept closed, and the wound area can be opened to a sufficient extent.

In addition, because the claw portions are comparatively deeply hung on the wound area entrance edge as described above, skin tissues around the wound area can certainly be pulled up only by lifting up the retractor, and a sufficient work space can be secured. Accordingly, the retractor of the present invention can suitably be used for formation of a work space in arthroscopic surgeries and so forth using an arthroscope in orthopedic surgery treatments.

In the above first aspect of the present invention, in a case where an overlapping direction of the first claw portions and the second claw portion in the closed state is set as a thickness direction of each of the first claw portions and the second claw portion, a thickness dimension of the first claw portion is preferably made smaller than a thickness dimension of the second claw portion.

For example, when the total thickness of the pair of first claw portions and the second claw portion is set as L, compared to a case where the thicknesses of the pair of first claw portions and the second claw portion are equivalently set to "L/3", in a case where the thicknesses of the pair of first claw portions are set to "L/4" and the thickness of the second claw portion is set to "L/2", a wound area can widely be stretched in the open state.

Further, a second aspect of the present invention provides a retractor abutting a wound area entrance edge of an incised skin tissue and opening the wound area, the retractor including: a plurality of first arm portions which are integrally coupled with each other on base end sides and extend toward tip ends; a plurality of second arm portions which are integrally coupled with each other on base end sides and are alternately arranged with the first arm portions, base end sides of the second arm portions being rotatably coupled with the first arm portions via a shaft portion, the second arm portions extending toward tip ends; and operation portions which perform opening and closing operations of the first arm portions and the second arm portions in a case where a state where the first arm portions and the second arm portions overlap with each other is set as a closed state and a state where tip end sides of the first arm portions and of the second arm portions are separated from each other is set as an open state, in which each of the first arm portions includes, in a tip end portion, a first claw portion which protrudes in an opening direction to be hung on the wound area entrance edge, each of the second arm portions includes, in a tip end portion, a second claw portion which protrudes in an opposite direction to the first claw portion to be hung on the wound area entrance edge, and when the first arm portions and the second arm portions are set to the closed state, the first claw portions and the second claw portions overlap with each other.

The retractor of the second aspect of the present invention includes two or more first claw portions in the tip end portions of two or more first arm portions, includes two or more second claw portions in the tip end portions of two or more second arm portions, and is thereby provided with four or more claw portions.

In the closed state, because the first claw portions and the second claw portions alternately overlap with each other, insertion into a wound area of an incised skin tissue can smoothly be performed.

When the first arm portions and the second arm portions start opening from the closed state by an operation of the operation portions, the first claw portions and the second claw portions become a hooked state where those are hooked on a wound area entrance edge in respective positions. In this case, because one claw portion is provided on the tip end portion of each of the arm portions, the arm portions do not obstruct a hanging state of each of the claw portions. Moreover, the claw portions protrude in the opening directions of the respective arm portions and thus become a state where those are comparatively deeply hung on the wound area entrance edge.

Furthermore, when the first arm portions and the second arm portions become the open state, the first claw portions and the second claw portions are separated in directions opposite to each other, and the wound area is thereby enlarged. In this case, because a plurality of first claw portions and a plurality of second claw portions abut the wound area entrance edge at respective positions, the wound area does not linearly extend while being kept closed, and the wound area can be opened to a sufficient extent.

In addition, because the claw portions are comparatively deeply hung on the wound area entrance edge as described above, skin tissues around the wound area can certainly be pulled up only by lifting up the retractor, and a sufficient work space can be secured. Accordingly, the retractor of the present invention can suitably be used for formation of a work space in arthroscopic surgeries and so forth using an arthroscope in orthopedic surgery treatments.

In the above second aspect of the present invention, in a case where an overlapping direction of the first claw portions and the second claw portions in the closed state is set as a thickness direction of each of the first claw portions and the second claw portions, thickness dimensions of at least a pair of claw portions which are positioned on outermost sides among the first claw portions and the second claw portions are preferably made smaller than thickness dimensions of the other claw portions.

For example, when the total thickness of a pair of first claw portions and a pair of second claw portions is set as L, compared to a case where the thicknesses of those are equivalently set to "L/4", in a case where the thicknesses of the pair of claw portions which are positioned on the outermost sides are set to "L/6" and the thicknesses of the pair of claw portions which are positioned on the inside are set to "L/3", a wound area can widely be stretched when the first arm portions and the second arm portions are set to the open state.

Further, in the first aspect or the second aspect of the present invention, tip ends of the first claw portions and tip ends of the second claw portions are preferably respectively directed in base end directions when the first arm portions and the second arm portion are in the open state compared to the closed state.

In such a manner, the first claw portions and the second claw portion can certainly be hung on a wound area entrance edge, and careless detachment of the first claw portions and the second claw portion from the wound area entrance edge can certainly be prevented when skin tissues around the wound area are pulled up.

In arthroscopic surgeries and so forth using an arthroscope in orthopedic surgery treatments, a formulation for treating a focal area in a work space can be injected into the work space which is formed by the retractor of the present invention. That is, the present invention also relates to a formulation which is injected into the work space formed by the retractor of the present invention and is for treating a focal area. The formulation for treating a focal area can be a formulation for caring damage to a cartilage of a joint of an articular cartilage or a base material for reproducing a defected cartilage (such as a sol composition of sodium alginate, see Japanese Patent No. 4740369), for example.

Further, in the first aspect or the second aspect of the present invention, the retractor may further include an opening maintaining device for maintaining an opening between the first arm portions and the second arm portion at a desired position. The opening maintaining device may include a locking member which extends in an opening-closing direction of a first operation rod portion and a second operation rod portion, a coupling portion which swingably couples the locking member with the first operation rod portion, a locking tooth which is provided on the second operation rod portion and is locked to the locking member in a releasable manner, and a finger handle portion which performs a swinging operation of the locking member.

The opening maintaining device in the above configuration is provided, the locking member and the locking tooth are thereby engaged together at a position where a desired opening is set which may include a state where the first arm portions and the second arm portion are closed (an opening of zero), and the opening can be maintained. Further, engagement with the locking tooth can easily be released by swinging the locking member. In particular, because the first arm portions and the second arm portion can be fixed to the closed state (an opening of zero), introduction work into a wound area and so forth become easy, for example.

DESCRIPTION OF EMBODIMENTS

Figure 1:
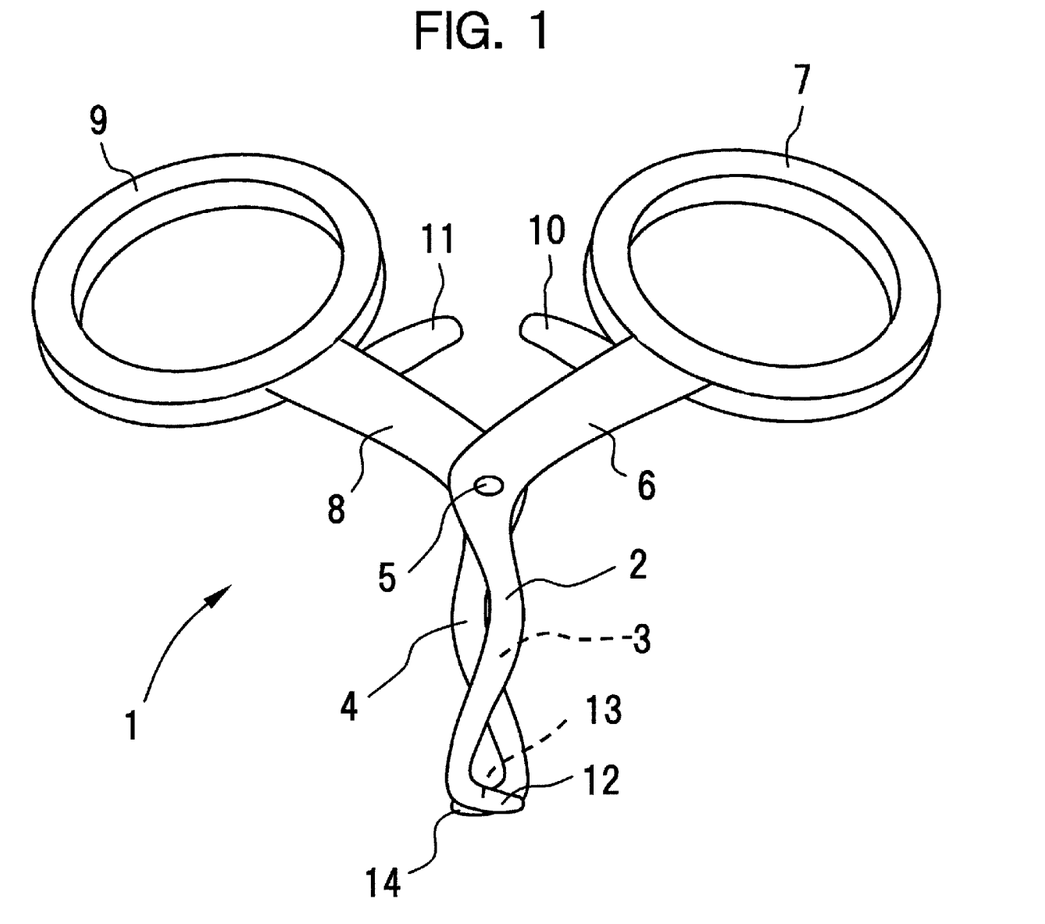
FIG. 1 is an explanatory perspective view illustrating a closed state of a retractor of a first embodiment of the present invention.
Figure 2:
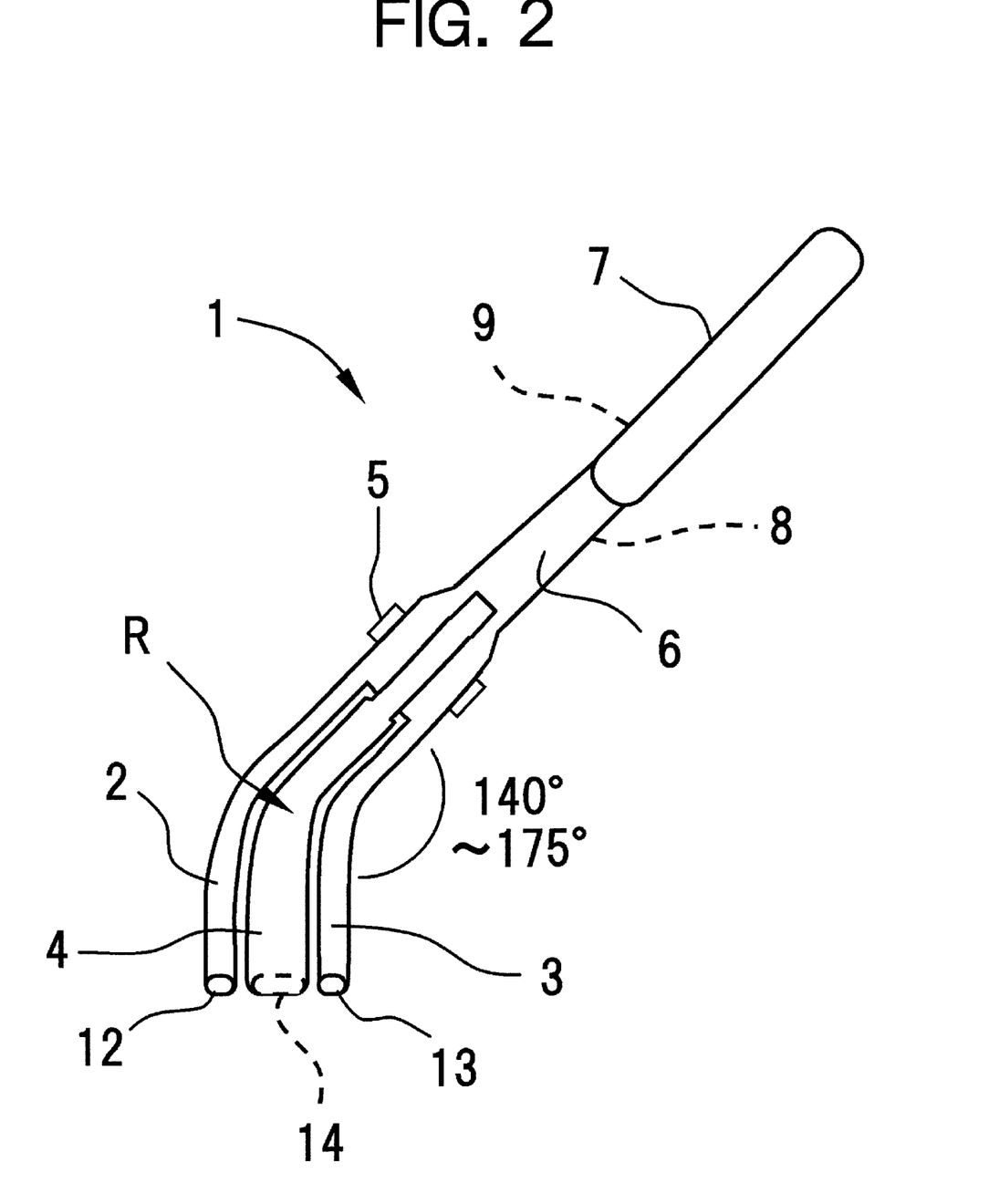
FIG. 2 is an explanatory side view of the retractor of the first embodiment.

A first embodiment of the present invention will be described with reference to FIG. 1 to FIG. 6. As illustrated in FIG. 1 and FIG. 2, a retractor 1 in the first embodiment includes two first arm portions 2 and 3 which are curved outward and one second aim portion 4 which is curved outward in the opposite direction to the first arm portions 2 and 3.

FIG. 1 and FIG. 2 illustrate the retractor 1 in a closed state. In the closed state, the second arm portion 4 is positioned between the first arm portions 2 and 3. In this case, the first arm portions 2 and 3 and the second arm portion 4 overlap with each other to partially intersect with each other. Further, as illustrated in FIG. 2, the first aim portions 2 and 3 and the second aim portion 4 are bent downward in the same direction from bent parts in intermediate positions in their longitudinal directions. A description will later be made about angles and so forth of the bent parts of the first arm portions 2 and 3 and the second arm portion 4.

As illustrated in FIG. 1 and FIG. 2, a shaft portion 5 is provided in a position on a base end side in which the first arm portions 2 and 3 and the second arm portion 4 overlap with each other. The shaft portion 5 rotatably couples the first arm portions 2 and 3 with the second aim portion 4 such that tip end sides are opened and closed.

On the opposite side to both of the first arm portions 2 and 3 via the shaft portion 5, a first operation rod portion 6 is provided, integrally with both of the first arm portions 2 and 3, to extend. A ring-shaped first finger handle portion 7 is provided on an end portion of the first operation rod portion 6.

On the opposite side to the second arm portion 4 via the shaft portion 5, a second operation rod portion 8 is provided, integrally with the second arm portion 4, to extend. A ring-shaped second finger handle portion 9 is provided on an end portion of the second operation rod portion 8.

Figure 3:
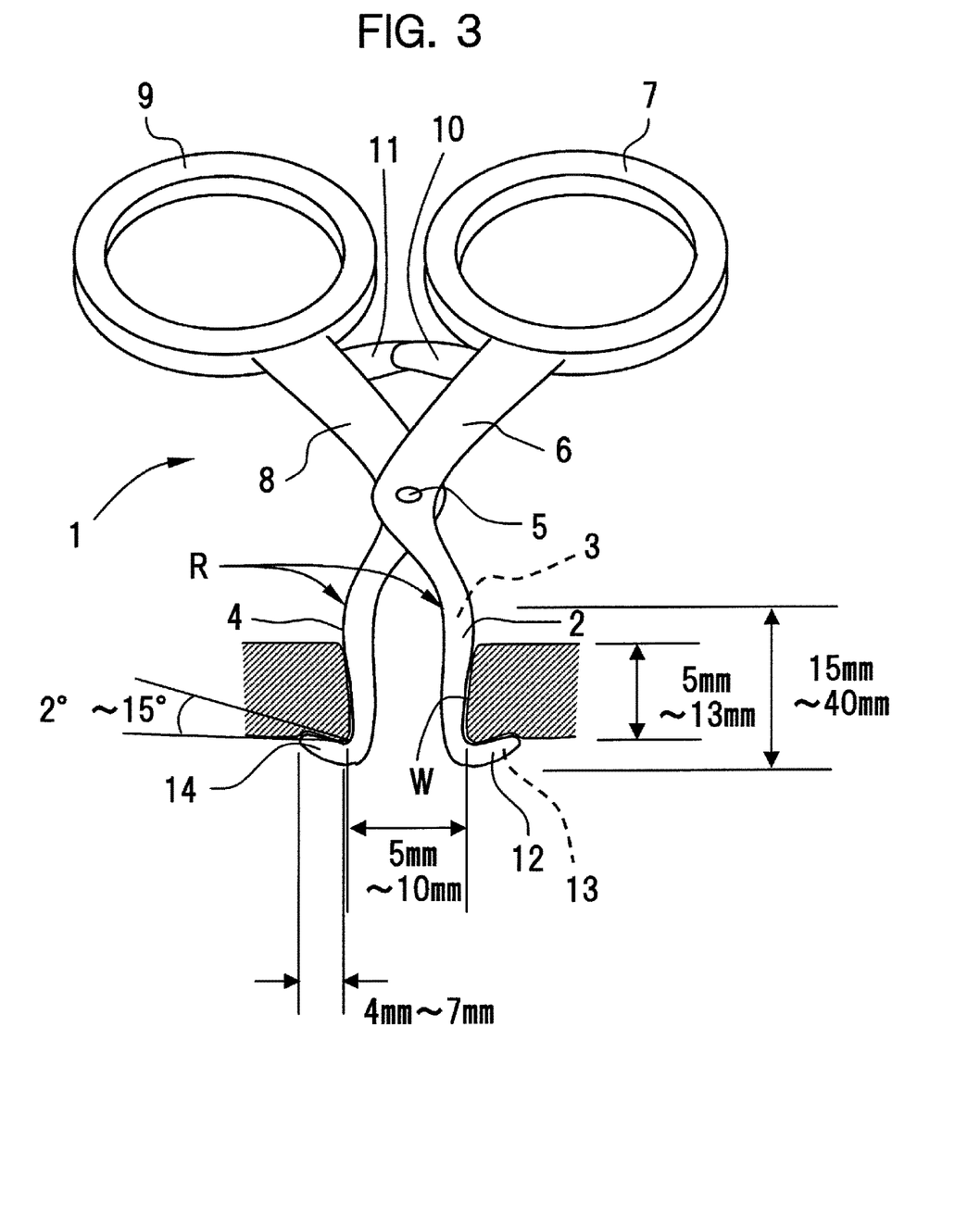
FIG. 3 is an explanatory perspective view illustrating an open state of the retractor of the first embodiment.

Fingers are respectively hooked on the first finger handle portion 7 and the second finger handle portion 9, the first operation rod portion 6 and the second operation rod portion 8 are moved in directions in which those approach each other, and the first arm portions 2 and 3 and the second arm portion 4 are thereby moved via the shaft portion 5 in directions in which those are separated away from each other and are set to an open state as illustrated in FIG. 3.

Note that the first operation rod portion 6 and first finger handle portion 7 and the second operation rod portion 8 and second finger handle portion 9 correspond to operation portions in the present invention.

Further, as an opening maintaining device for maintaining an open or closed state of the first arm portions 2 and 3 and the second arm portion 4, a first locking tooth portion 10 is provided on the first operation rod portion 6, and a second locking tooth portion 11 is provided on the second operation rod portion 8.

The first locking tooth portion 10 and the second locking tooth portion 11 are meshed with each other in a releasable manner and maintain an open state of the first arm portions 2 and 3 and the second arm portion 4 as illustrated in FIG. 3. Meshing between the first locking tooth portion 10 and the second locking tooth portion 11 can easily be released by applying a force to the first operation rod portion 6 and the second operation rod portion 8 in a direction opposite to a superimposing direction and by causing distortion between the first operation rod portion 6 and the second operation rod portion 8.

Note that the opening maintaining device for maintaining an open state of the first arm portions 2 and 3 and the second arm portion 4 is not limited to a configuration in which the first locking tooth portion 10 of the first operation rod portion 6 and the second locking tooth portion 11 of the second operation rod portion 8 are meshed with each other.

Figure 4:
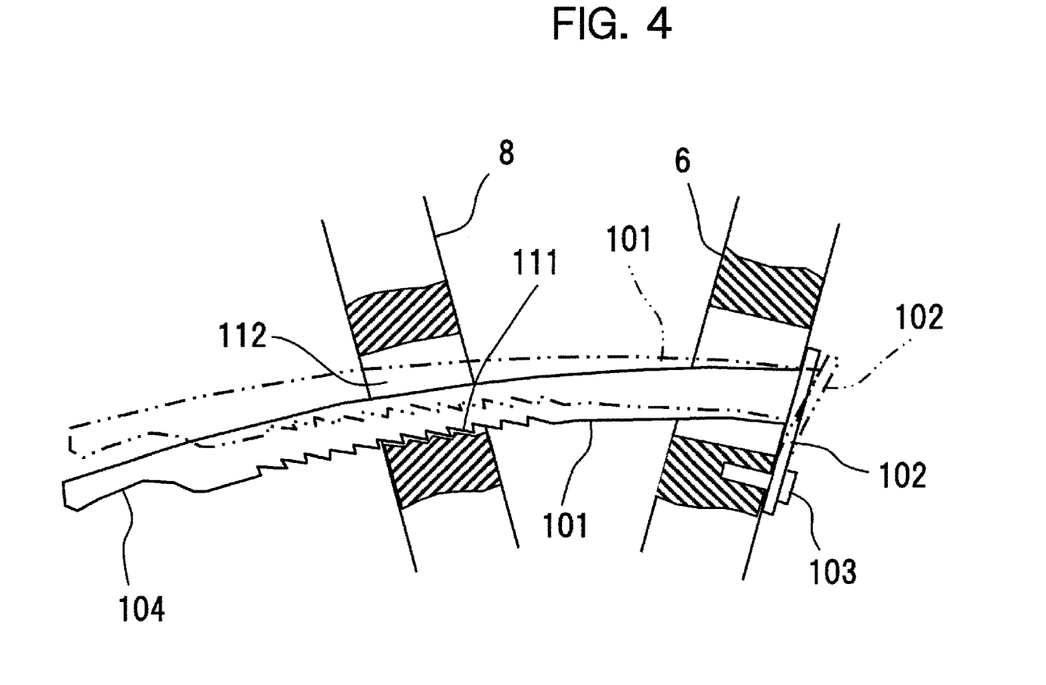
FIG. 4 is an explanatory diagram illustrating a variation of an opening maintaining device.

As another opening maintaining device, for example, an opening maintaining device illustrated in FIG. 4 can be raised. The opening maintaining device illustrated in FIG. 4 can fix the first arm portions 2 and 3 and the second arm portion 4 even in a state where those are closed.

That is, as illustrated in FIG. 4, the other opening maintaining device includes a locking member 101 which extends in an opening-closing direction while passing through the first operation rod portion 6 and the second operation rod portion 8. A coupling portion 102 is provided on a base end portion of the locking member 101, and the coupling portion 102 is fixed to the first operation rod portion 6 by a rivet 103. Locking teeth 111 to which the locking member 101 is locked are formed in a through hole 112 of the second operation rod portion 8, through which the locking member 101 passes. A finger handle portion 104 is formed in a tip end portion of the locking member 101.

The locking member 101 is urged in a direction toward the locking teeth 111 by elasticity of the coupling portion 102. When an operation is made in a direction to close the first operation rod portion 6 and the second operation rod portion 8 (a direction to increase the opening between the first arm portions 2 and 3 and the second arm portion 4), the locking member 101 overcomes the locking teeth 111 in a bumping manner, and the opening between the first arm portions 2 and 3 and the second arm portion 4 is thereby maintained. Meanwhile, when an operation is made in a direction to open the first operation rod portion 6 and the second operation rod portion 8 (a direction to decrease the opening between the first arm portions 2 and 3 and the second arm portion 4), the locking member 101 is swung by hooking a finger on the finger handle portion 104, and locking of the locking member 101 to the locking teeth 111 can thereby be released.

As illustrated in FIG. 1 to FIG. 3, first claw portions 12 and 13 are formed in respective tip end portions of the two first arm portions 2 and 3. The two first claw portions 12 and 13 are provided to protrude with their tip ends being directed in an opening direction.

A second claw portion 14 is formed in a tip end portion of the second arm portion 4. The second claw portion 14 is provided to protrude with its tip end being directed in the opening direction. That is, the second claw portion 14 protrudes in the opposite direction to the first claw portions 12 and 13.

Figure 5:
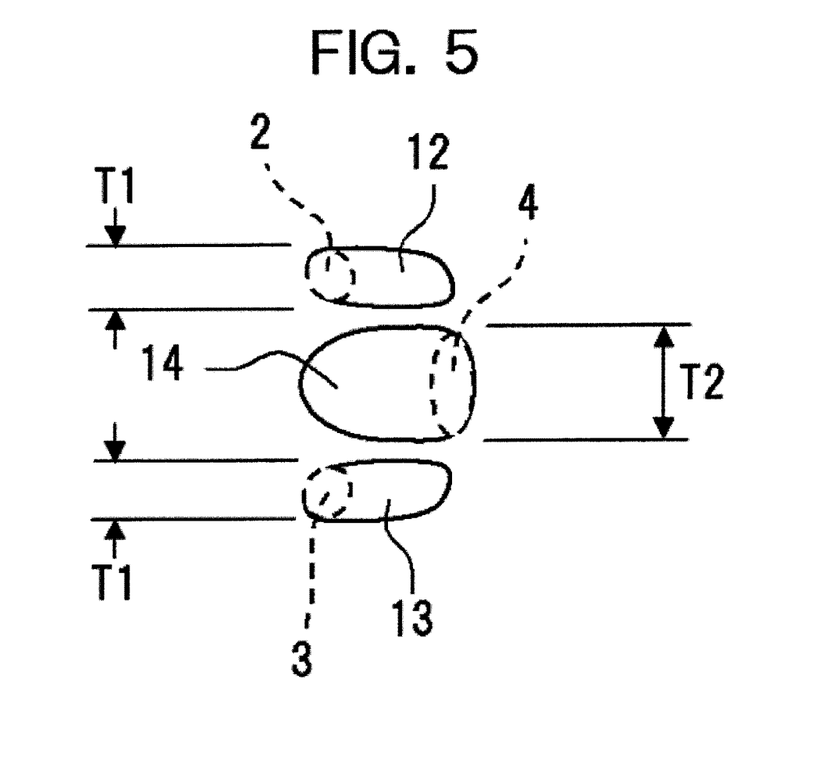
FIG. 5 is an explanatory diagram illustrating claw portions in the closed state of the retractor of the first embodiment.

As illustrated in FIG. 5, in the closed state, the second claw portion 14 is positioned between the first claw portions 12 and 13, and those are superimposed on each other and are thereby compactly gathered.

In addition, as illustrated in FIG. 5, the first claw portions 12 and 13 which are positioned on the outside of the second claw portion 14 are smaller than the second claw portion 14. Specifically, when it is assumed that a dimension in an overlapping direction of the first claw portions 12 and 13 and the second claw portion 14 in the closed state is set as a thickness dimension, a dimension T1 of each of the first claw portions 12 and 13 in a thickness direction is smaller than a dimension T2 of the second claw portion 14 in the thickness direction. Accordingly, tip end portions (the first claw portions 12 and 13 and the second claw portion 14) of the retractor 1 can smoothly be inserted into a wound area of a skin tissue which is incised comparatively small. Further, as described above, the dimension T1 of each of the first claw portions 12 and 13 in the thickness direction is made smaller than the dimension T2 of the second claw portion 14 in the thickness direction, and a wound area in an open state can thereby widely be stretched.

When the tip end portions are inserted into the wound area and the first arm portions 2 and 3 and the second arm portion 4 are opened, the first claw portions 12 and 13 and the second claw portion 14 become a hooked state where those are hooked on a wound area entrance edge. Then, in an open state, respective base end portions of the first claw portions 12 and 13 and the second claw portion 14 (boundary parts between the first arm portions 2 and 3 and the first claw portions 12 and 13 and a boundary part between the second arm portion 4 and the second claw portion 14) abut the wound area entrance edge, pull each other, and thereby sets the wound area to an opened state.

Figure 6:
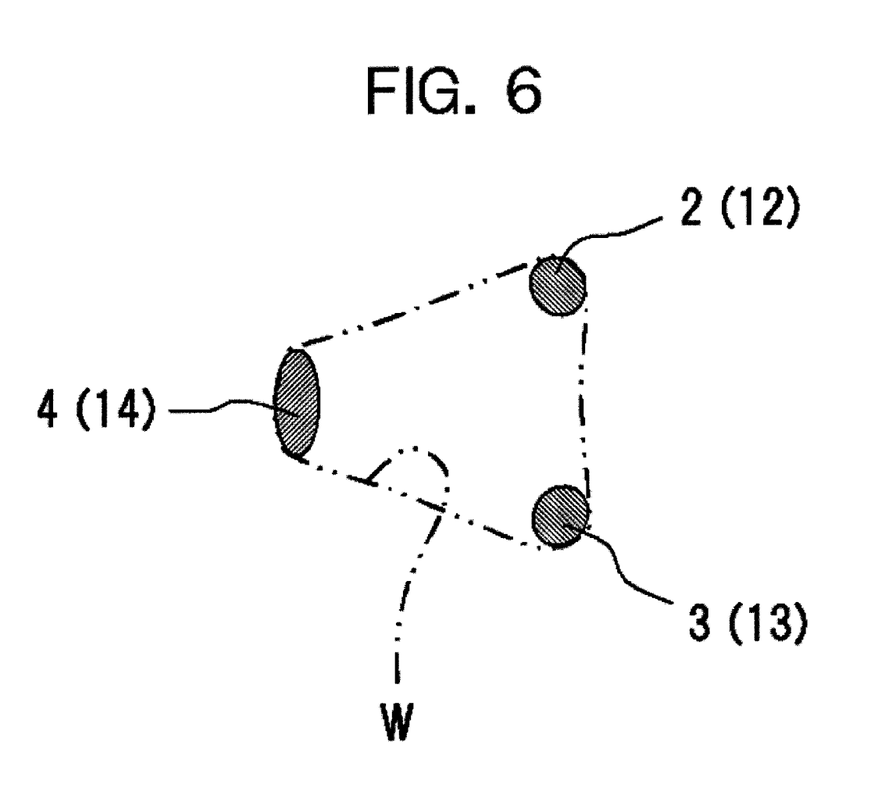
FIG. 6 is an explanatory diagram illustrating base end portion positions of the claw portions in the open state of the retractor of the first embodiment.

In this case, as FIG. 6 illustrates the first arm portions 2 and 3 (the base end portions of the first claw portions 12 and 13) and the second arm portion 4 (the base end portion of the second claw portion 14) in a cross-sectional view, the first arm portions 2 and 3 as the base end portions of the first claw portions 12 and 13 and the second arm portion 4 as the base end portion of the second claw portion 14 abut respective positions of a wound area entrance edge W and spread the wound area in three directions. In such a manner, without the wound area linearly extending in a closed state, a state can be maintained where the wound area is sufficiently expanded.

Further, as illustrated in FIG. 5 and FIG. 6, each of cross-sectional shapes of the first arm portions 2 and 3 (the base end portions of the first claw portions 12 and 13) is formed into an ellipse which is inclined at a predetermined angle. Thus, as illustrated in FIG. 6, corner angle portions of the expanded wound area entrance edge W become gentle, the corner angle portions contacting with the first arm portions 2 and 3 (the base end portions of the first claw portions 12 and 13), and a load on the wound area entrance edge W in expansion is thereby reduced. Note that each of the cross-sectional shapes of the first arm portions 2 and 3

(the base end portions of the first claw portions 12 and 13) is not limited to this but may be formed into an ellipse which is not inclined.

Further, when the first arm portions 2 and 3 and the second arm portion 4 are opened (separated away from each other), the tip end portions of the first arm portions 2 and 3 and the tip end portion of the second arm portion 4 respectively draw circular arc loci. Thus, the tip end of each of the claw portions 12, 13, and 14 in an open state is directed in a base end direction (upward in FIG. 3) compared to the closed state. Accordingly, a state where each of the claw portions 12, 13, and 14 is hung on the wound area entrance edge is further certainly maintained.

In addition, as illustrated in FIG. 3, in an open state, the first claw portions 12 and 13 protrude such that at least their tip end portions are positioned on the outside of the first arm portions 2 and 3. Similarly, the second claw portion 14 protrudes such that at least its tip end portion is positioned on the outside of the second arm portion 4. In such a manner, when the first claw portions 12 and 13 and the second claw portion 14 are hung on a wound area entrance edge, each of the arm portions 2, 3, and 4 does not become an obstacle. Thus, the first claw portions 12 and 13 and the second claw portion 14 can deeply be hung on a wound area entrance edge. Furthermore, the retractor 1 is pulled up which opens the wound area in a state where the first claw portions 12 and 13 and the second claw portion 14 are hung on the wound area entrance edge, skin tissues around the wound area are thereby caused to follow the retractor 1, and a work space with a sufficient extent can be secured on the inside of skin tissues.

In order to pull up the retractor 1 which opens the wound area while the wound area is observed from above, it is desirable that the first finger handle portion 7 and the second finger handle portion 9 not be positioned right above the wound area. Meanwhile, in order to reduce loads applied to fingers by the first finger handle portion 7 and the second finger handle portion 9 when the retractor 1 is pulled up, it is desirable that a pulling-up direction generally agree with directions of the first arm portions 2 and 3 and the second arm portion 4. Furthermore, in order to realize both of visibility of the wound area and pulling-up operability as conditions which mutually conflict in such a manner, it is desirable that an angle of a bent part R of the arm portions 2, 3, and 4 (a depression angle of an extended line of insertion regions of the arm portions 2, 3, and 4 into the wound area with respect to an extended line of the operation rod portions 6 and 8 in a side view), which is illustrated in FIG. 2, be set to 140° to 175°.

Note that in order to further improve visibility of the wound area in an angle range of the above bent part R, although not illustrated, the operation rod portions 6 and 8 may be formed to have comparatively long dimensions. Alternatively, although not illustrated, the above-described bent part R may be formed into a crank shape in a side view, and extension directions of the arm portions 2, 3, and 4 may thereby be offset from directions in which the operation rod portions 6 and 8 extend.

Further, as illustrated in FIG. 3, a length of each of the claw portions 12, 13, and 14 is preferably 4 to 7 mm, and angles of the first claw portions 12 and 13 with respect to the first arm portions 2 and 3 and an angle of the second claw portion 14 with respect to the second arm portion 4 are preferably set to 2° to 15°.

The length of each of the claw portions corresponds to the relative relationship between a thickness of a skin tissue and a size of a small incision. A thickness of skin is in general 5 to 13 mm (epidermis+dermis: 1 to 4 mm and hypodermal tissue: 4 to 9 mm). The size of a small incision is 5 to 10 mm. A width of the wound area in an open state of the retractor 1, which is illustrated in FIG. 3, becomes 5 to 10 mm because a tension is applied to the wound area entrance edge W. In order to hang the claw portions 12, 13, and 14 on a wound area entrance edge at this size and to lift a tissue at a thickness of 5 to 13 mm, the lengths of the claw portions 12, 13, and 14 are preferably 4 to 7 mm, and the angles of the first claw portions 12 and 13 with respect to the first arm portions 2 and 3 and the angle of the second claw portion 14 with respect to the second arm portion 4 are preferably set to 2° to 15°.

In addition, as illustrated in FIG. 3, the first arm portions 2 and 3 and the second arm portion 4 are formed to have appropriate lengths, and lengths from the bent portion R to the tip ends in the first arm portions 2 and 3 and the second arm portion 4 are preferably set to 15 to 40 mm and further preferably set to 30 to 40 mm. The thickness of skin is in general 5 to 13 mm (epidermis+dermis: 1 to 4 mm and hypodermal tissue: 4 to 9 mm) as described above. The lengths of the first arm portions 2 and 3 and the second arm portion 4 are set to 15 to 40 mm, sufficient introduction depths of the first arm portions 2 and 3 and the second arm portion 4 into a wound area can thereby be obtained, and operability in locking the claw portions 12, 13, and 14 under skin is improved.

Next, a second embodiment of the present invention will be described with reference to FIG. 7 to FIG. 9. Note that the same reference characters as FIG. 1 to FIG. 6 are given to similar configurations to the above first embodiment, and descriptions thereof will not be made. The second embodiment as illustrated in FIG. 7 may include an opening maintaining device as illustrated in FIG. 4.

Figure 7:
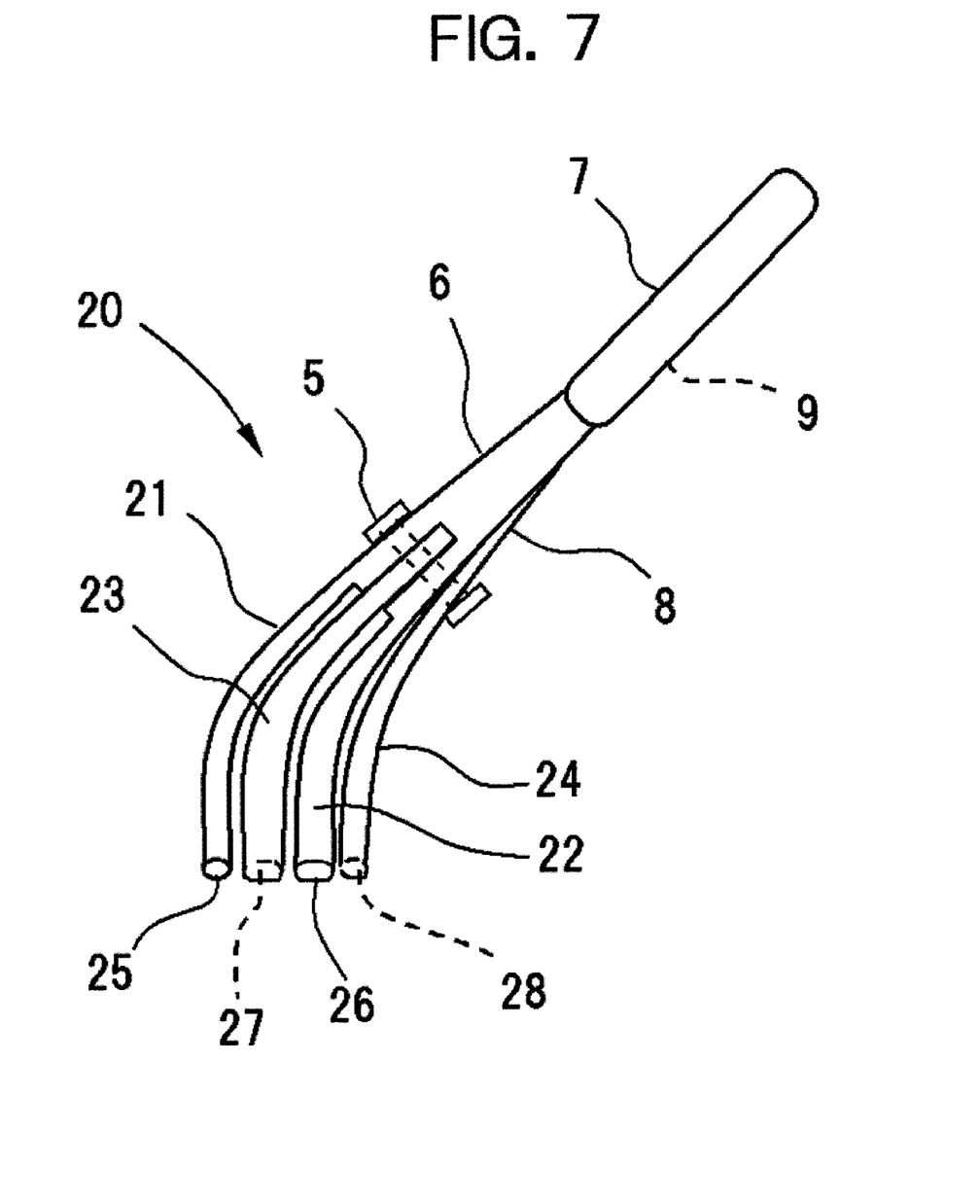
FIG. 7 is an explanatory side view illustrating a closed state of a retractor of a second embodiment of the present invention.

As illustrated in FIG. 7 in a side view, a retractor 20 of the second embodiment includes two first arm portions 21 and 22 and two second arm portions 23 and 24.

Figure 8:
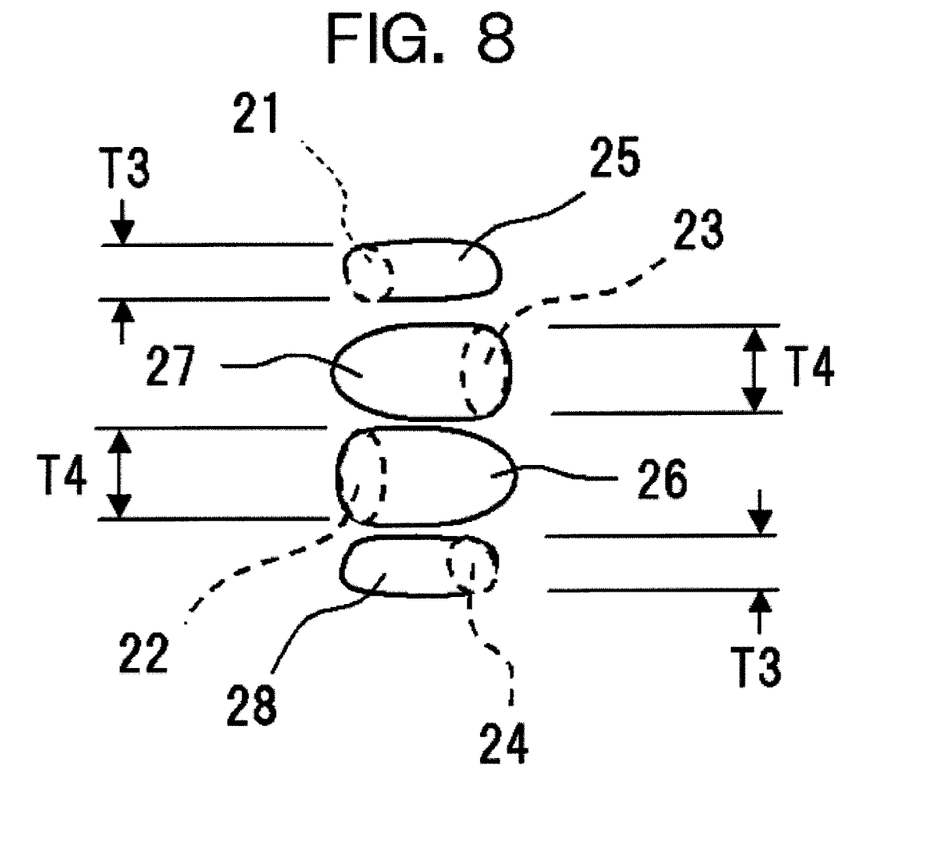
FIG. 8 is an explanatory diagram illustrating claw portions in the closed state of the retractor of the second embodiment.

As illustrated in FIG. 8, first claw portions 25 and 26 are formed in respective tip end portions of the two first arm portions 21 and 22. The two first claw portions 25 and 26 are provided to protrude with their tip ends being directed in an opening direction. Second claw portions 27 and 28 are formed in respective tip end portions of the two second arm portions 23 and 24. The two second claw portions 27 and 28 are provided to protrude with their tip ends being directed in an opening direction.

In a closed state, the first claw portions 25 and 26 and the second claw portions 27 and 28 are alternately positioned, are superimposed on each other, and become a compactly gathered state.

In addition, as illustrated in FIG. 8, the first claw portion 25 and the second claw portion 28 which are positioned on the outermost sides are smaller than the other first claw portion 26 and second claw portion 27. That is, when it is assumed that a dimension in an overlapping direction of the first claw portions 25 and 26 and the second claw portions 27 and 28 in the closed state is set as a thickness dimension, respective dimensions T3 of the first claw portion 25 and the second claw portion 28, which are positioned on the outermost sides, in a thickness direction are smaller than respective dimensions T4 of the first claw portion 26 and the second claw portion 27, which are other than those (positioned on the inside), in the thickness direction.

When the tip end portions are inserted into a wound area and the first arm portions 21 and 22 and the second arm portions 23 and 24 are opened, the first claw portions 25 and 26 and the second claw portions 27 and 28 become a hooked state where those are hooked on a wound area entrance edge. Then, as illustrated in FIG. 9, in an open state, the first arm portions 21 and 22 as base end portions of the first claw portions 25 and 26 and the second arm portions 23 and 24 as base end portions of the second claw portions 27 and 28 abut respective positions of a wound area entrance edge W and spread the wound area in four directions. In such a manner, without the wound area linearly extending in a closed state, a state can be maintained where the wound area is sufficiently expanded.

Furthermore, the retractor 20 is pulled up in a state where the first claw portions 25 and 26 and the second claw portions 27 and 28 are deeply hung on the wound area entrance edge, skin tissues around the wound area are thereby caused to follow the retractor 20, and a work space with a sufficient extent can be secured on the inside of skin tissues.

Figure 9:
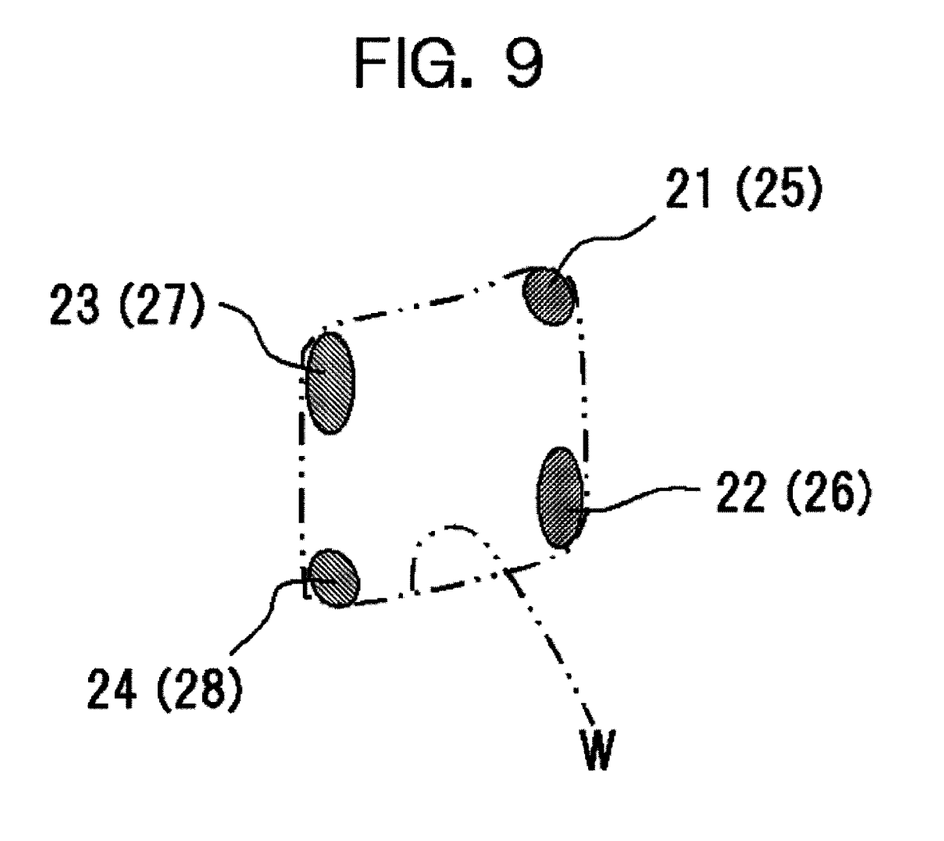
FIG. 9 is an explanatory diagram illustrating base end portion positions of the claw portions in an open state of the retractor of the second embodiment.

Further, as illustrated in FIG. 8 and FIG. 9, each of cross-sectional shapes of the first arm portion 21 (the base end portion of the first claw portion 25) and the second arm portion 24 (the base end portion of the second claw portion 28), which are positioned on the outside, is formed into an ellipse which is inclined at a predetermined angle. Thus, as illustrated in FIG. 9, corner angle portions of the expanded wound area entrance edge W become gentle, the corner angle portions contacting with the first arm portion 21 (the base end portion of the first claw portion 25) and the second arm portion 24 (the base end portion of the second claw portion 28), and a load on the wound area entrance edge W in expansion is thereby reduced. Note that each of the cross-sectional shapes of the first arm portion 21 (the base end portion of the first claw portion 25) and the second arm portion 24 (the base end portion of the second claw portion 28) is not limited to this but may be formed into an ellipse which is not inclined.

Further, as described above, the respective dimensions T3 of the first claw portion 25 and the second claw portion 28, which are positioned on the outside, in the thickness direction are smaller than respective dimensions T4 of the first claw portion 26 and the second claw portion 27, which are positioned on the inside, in the thickness direction (see FIG. 8). In such a manner, when the first arm portions and the second arm portions are set to an open state, a wound area can widely be stretched compared to a case where thickness dimensions of all of the first claw portions and all of the second claw portions are the same.

Figure 10A:
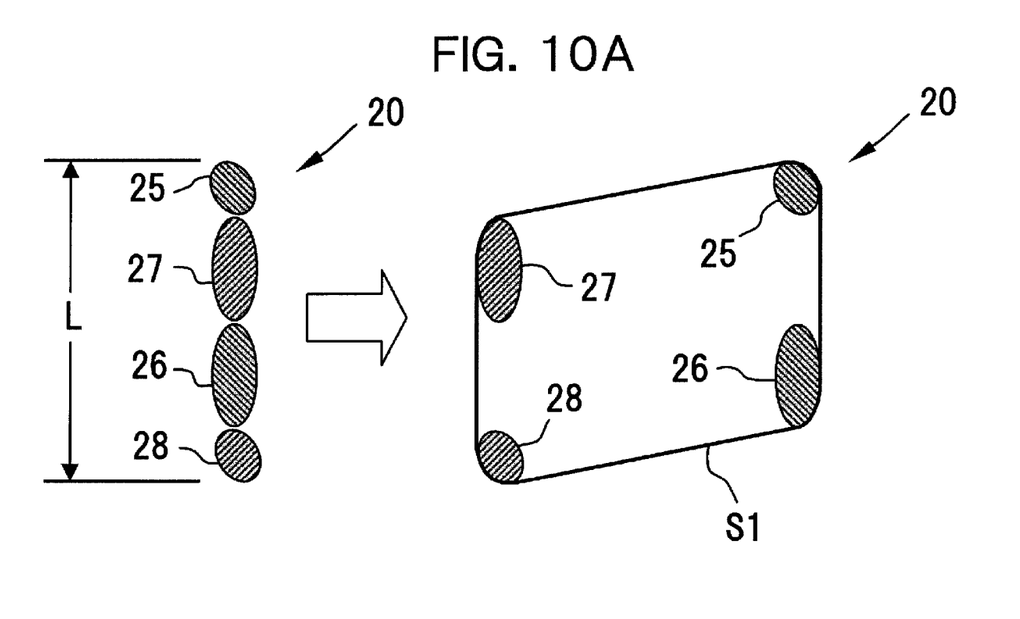
FIG. 10A is a diagram schematically illustrating the thickness of each of the claw portions of the retractor of the second embodiment.
Figure 10B:
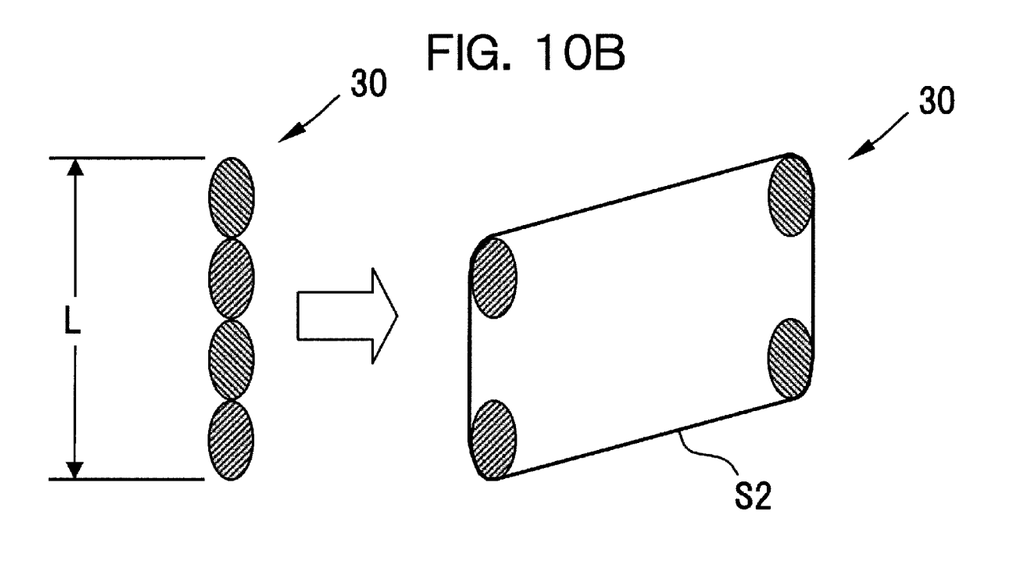
FIG. 10B is a diagram schematically illustrating the thickness of each claw portion of a retractor of a comparative example.

This will be described in detail with reference to FIG. 10A to FIG. 10C which schematically illustrate the size relationship among the claw portions. FIG. 10A schematically illustrates a case where the thickness dimensions of the claw portions 25 and 28 on the outside are smaller than those of the claw portions 26 and 27 on the inside (the retractor 20 of the second embodiment). FIG. 10B schematically illustrates a case where the thickness dimensions of all claw portions are the same (comparative example 30). In both of those cases, a distance dimension L between both ends in the thickness direction are the same.

Figure 10C:
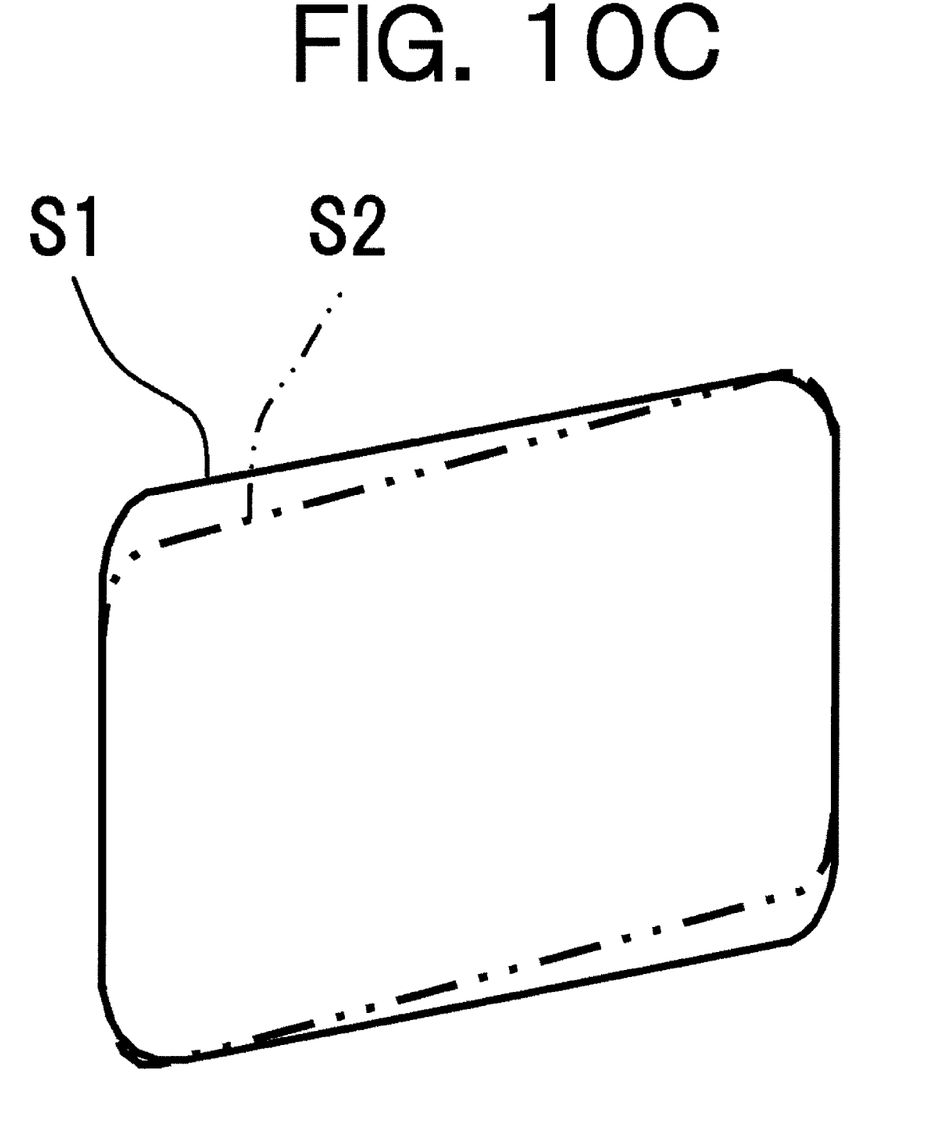
FIG. 10C is a diagram for comparing expanded shapes between the claw portions of the retractor of the second embodiment and claw portions of the retractor of the comparative example.

Here, when the claw portions are expanded and the areas in those expanded shapes are compared, as illustrated in FIG. 10C by causing both expanded shapes S1 and S2 to overlap with each other, the area of the expanded shape S1 by the retractor 20 of the second embodiment is larger than the area of the expanded shape S2 by the comparative example 30.

As described above, the retractor 20 of the second embodiment can comparatively widely stretch a wound area and can thus obtain high workability.

Further, also in the retractor 20 of the second embodiment, in order to certainly obtain the above effects, a length of each of the claw portions 25, 26, 27, and 28 is preferably 4 to 7 mm, and angles of the first claw portions 25 and 26 with respect to the first arm portions 21 and 22 and angles of the second claw portions 27 and 28 with respect to the second arm portions 23 and 24 are preferably set to 2° to 15°.

Note that in the second embodiment, the retractor 20 is raised which includes the two first arm portions 21 and 22 and the two second arm portions 23 and 24; however, the numbers of first arm portions and second arm portions are not limited to those, and it is possible to provide two or more first arm portions and two or more second arm portions.

Further, in the above embodiments, as illustrated in FIG. 2 and FIG. 7, descriptions are made by raising the first arm portions 2, 3, 21, and 22 and second arm portions 4, 23, 24 which are bent downward in the same direction at intermediate positions in their longitudinal directions. However, a retractor of the present invention is not limited to those, and for example, although not illustrated, the first arm portion and the second arm portion may linearly extend toward tip ends.

As described in the foregoing, a work space with a sufficient extent can be secured on the inside of skin tissues by using the retractor of the present invention. A formulation for treating a focal area can be injected into the secured work space. The formulation for treating a focal area can be a formulation for caring damage to a cartilage of a joint of an articular cartilage or a base material for reproducing a defected cartilage (such as a sol composition of sodium alginate, see Japanese Patent No. 4740369), for example.

INDUSTRIAL APPLICABILITY

A retractor of the present invention has a configuration which can easily form a work space for arthroscopic surgery in a state where a wound area is spread and can thereby suitably be used as a medical tool.

REFERENCE SIGNS LIST 1, 20 retractor
2, 3, 21, 22 first arm portion
4, 23, 24 second arm portion
12, 13, 25, 26 first claw portion
14, 27, 28 second claw portion
6 first operation rod portion (operation portion)
7 first finger handle portion (operation portion)
8 second operation rod portion (operation portion)
9 second finger handle portion (operation portion)
101 locking member
102 coupling portion
104 finger handle portion
111 locking teeth

The invention claimed is:

1. A retractor for abutting edges of a wound area entrance of an incised skin tissue and opening the wound area entrance, the retractor comprising:
   a pair of first arm portions which are integrally coupled with each other on a first base end portion and extend toward first tip end portions respectively;
   a single second arm portion which has a second base end portion and extend toward a second tip end portion;
   a shaft portion which is provided at a position where the first base end portion of the first arm portions overlaps with the second base end portion of the second arm portion to rotatably couple the first arm portions and the second arm portion so as to enable the first arm portions and the second arm portion to open and close, wherein the first arm portions and the second arm portion are configured to overlap with each other between the shaft portion and the first and the second tip end portions in a closed state of the first arm portions and the second arm portion;

first claw portions rounded which are formed at the first tip end portions of the first arm portions respectively and outwardly protrude therefrom respectively to be hung on one edge of the edges of the wound area entrance;

a second claw portion rounded which is formed outwardly protruding from the second tip end portion of the second arm portion in opposite direction to the first claw portions so as to be hung on another edge of the edges of the wound area entrance, wherein the second claw portion is configured to overlap with the first claw portions in the closed state of the first arm portions and the second arm portion; and operation portions which are provided integrally with the first arm portions and the second arm portion via the first base end portion and the second base end portion respectively to perform opening and closing operations of the first arm portions and the second arm portion, where a state where the first tip end portions of the first arm portions and the second tip end portion of the second arm portion are separated from each other is set as an open state to open the wound area entrance.

2. The retractor according to claim 1, wherein the first claw portions and the second claw portion are configured so that a thickness of each of the first claw portions is made smaller than a thickness of the second claw portion in a thickness direction in the closed state, where the thickness direction is a direction in which the first claw portions and the second claw portion overlap with each other in the closed state.

3. The retractor according to claim 1, wherein tip ends of the first claw portions and a tip end of the second claw portion are respectively directed in base end directions when the first arm portions and the second arm portion are in the open state compared to the closed state.

4. The retractor according to claim 1, further comprising an opening maintaining device for maintaining an opening between the first arm portions and the second arm portion at a desired position, wherein the opening maintaining device includes a locking member which extends in an opening closing direction of a first operation rod portion and a second operation rod portion, a coupling portion which swingably couples the locking member with the first operation rod portion, a locking tooth which is provided on the second operation rod portion and is locked to the locking member in a releasable manner, and a finger handle portion which performs a swinging operation of the locking member.

5. A method for opening a wound area comprising:
providing the retractor of claim 1;
inserting the first claw portions and the second claw portion of the retractor of claim 1 into the wound entrance; and then
causing the first claw portions to move away from the second claw portion to open the wound entrance.

6. A retractor for abutting edges of a wound area entrance of an incised skin tissue and opening the wound area entrance, the retractor comprising:

a plurality of first arm portions which are integrally coupled with each other on a first base end portion and extend toward first tip end portions respectively;

one or more second arm portions which are integrally coupled with each other on a second base end portion and extend toward second tip end portions respectively;

a shaft portion which is provided at a position where the first base end portion of the first arm portions overlaps with the second base end portion of the one or more second arm portions to rotatably couple the first arm portions and the one or more second arm portions so as to enable the first arm portions and the one or more second arm portions to open and close, wherein the first arm portions and the one or more second arm portions are configured to overlap with each other between the shaft portion and the first and the second tip end portions in a closed state of the first arm portions and the one or more second arm portions;

first claw portions rounded which are formed outwardly protruding from the first tip end portions of the first arm portions respectively so as to be hung on one edge of the edges of the wound area entrance;

one or more second claw portions rounded which are formed outwardly protruding from the second tip end portions of the one or more second arm portions in opposite directions to the first claw portions respectively so as to be hung on another edge of the edges of the wound area entrance, wherein the one or more second claw portions are configured to overlap with the first claw portions respectively in the closed state of the first arm portions and the one or more second arm portions; and operation portions which are provided integrally with the first arm portions and the one or more second arm portion via the first base end portion and the second base end portion respectively to perform opening and closing operations of the first arm portions and the one or more second arm portions, where a state where the first tip end portions of the first arm portions and the second tip end portions of the one or more second arm portions are separated from each other is set as an open state to open the wound area entrance.

7. The retractor according to claim 6, wherein the first claw portions and the second claw portions are configured so that each thickness of at least a pair of claw portions which are positioned on outermost sides among the first claw portions and the second claw portions is smaller than each thickness of the other claw portions in a thickness direction in the closed state, where the thickness direction is a direction in which the first claw portions and the second claw portions overlap with each other in the closed state.

8. The retractor according to claim 6, wherein tip ends of the first claw portions and tip ends of the second claw portions are respectively directed in base end directions when the first arm portions and the second arm portions are in the open state compared to the closed state.

9. The retractor according to claim 6, further comprising an opening maintaining device for maintaining an opening between the first arm portions and the second arm portions at a desired position, wherein the opening maintaining device includes a locking member which extends in an opening closing direction of a first operation rod portion and a second operation rod portion, a coupling portion which swingably couples the locking member with the first operation rod portion, a locking tooth which is provided on the second operation rod portion and is locked to the locking member in a releasable manner, and a finger handle portion which performs a swinging operation of the locking member.

10. A method for opening a wound area comprising:
providing the retractor of claim 6;
inserting the first claw portions and the second claw portions of the retractor of claim 6 into the wound entrance; and then
causing the first claw portions to move away from the second claw portions to open the wound entrance.

\* \* \* \* \*